Figure 1:
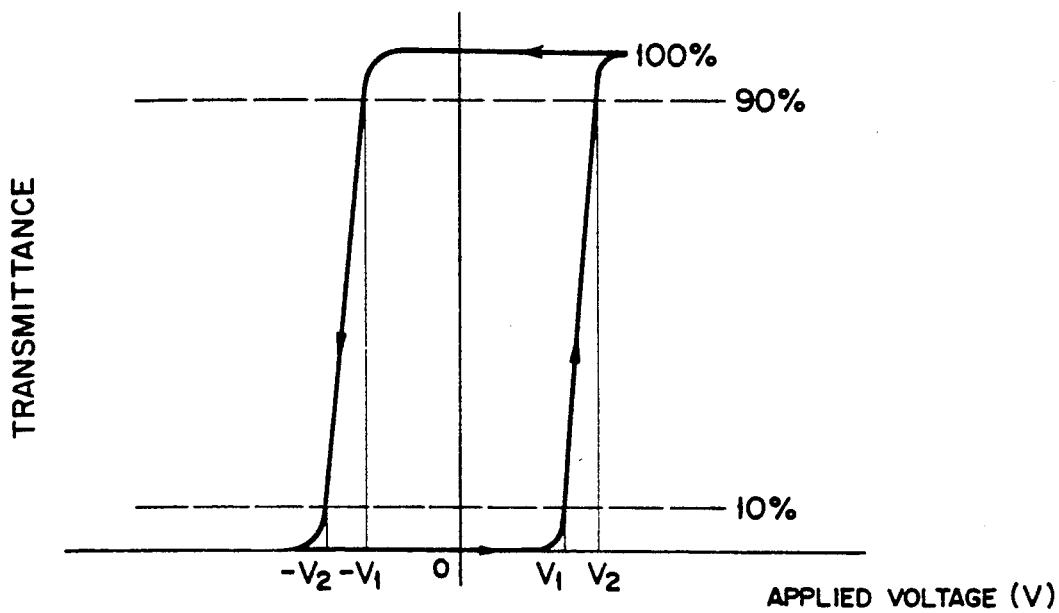

United States Patent [19]

Hagiwara et al.

[11] Patent Number: 5,130,050

[45] Date of Patent: Jul. 14, 1992

[54] LIQUID CRYSTAL COMPOUND

[75] Inventors: Takashi Hagiwara; Noriko Yamakawa; Ichiro Kawamura, all of Tokyo, Japan

[73] Assignee: Showa Shell Sekiyo Kabushiki Kaisha, Tokyo, Japan

[21] Appl. No.: 599,849

[22] Filed: Oct. 19, 1990

[30] Foreign Application Priority Data

Oct. 27, 1989 [JP] Japan ................... 1-281120

[51] Int. Cl.[5] ................... C09K 19/12; C07C 69/76
[52] U.S. Cl. .................. 252/299.65; 252/299.01; 560/59; 560/73; 560/76; 560/86; 560/102; 560/108
[58] Field of Search .......... 252/299.01, 299.6, 299.62, 252/299.64, 299.66, 299.67; 560/59, 73, 76, 86, 102, 108

[56] References Cited

U.S. PATENT DOCUMENTS

| | | | |
|---|---|---|---|
| 4,576,732 | 3/1986 | Isogai et al. | 252/299.65 |
| 4,728,458 | 3/1988 | Higuchi et al. | 252/299.65 |
| 4,753,752 | 6/1988 | Raynes et al. | 252/299.65 |
| 4,867,903 | 9/1988 | Nohira et al. | 252/299.61 |
| 4,918,213 | 7/1989 | Nohira et al. | 558/271 |
| 4,921,632 | 8/1989 | Nakamura et al. | 252/299.1 |
| 4,931,208 | 6/1990 | Furukawa et al. | 252/299.61 |

FOREIGN PATENT DOCUMENTS

| | | |
|---|---|---|
| 0191600 | 8/1986 | European Pat. Off. . |
| 327349 | 8/1989 | European Pat. Off. . |
| 334628 | 9/1989 | European Pat. Off. . |
| 63-161005 | 7/1988 | Japan . |
| 1-213390 | 8/1989 | Japan . |

OTHER PUBLICATIONS

Suzuki et al., Fluorine-Containing Ferroelectric Liquid Crystal Compound Showing Tristable Switching, Second Int'l Conf. on Ferroelectric Liquid Crystals Abstract PI06 (Jun. 27-30, 1989).

Yamawaki et al., 3.3 Electro-Optical Properties of Fluorine-Containing Ferroelectric Liquid Crystal Cells, Proceedings of the Ninth Int'l Display Research Conf. 26 (Oct. 16-18, 1989).

Suzuki et al., New Fluorine-Containing Ferroelectric Liquid Crystal Compounds With Large Spontaneous Polarization And Fast Switching Time, Twelfth Int'l Liquid Crystal Conf. Abstract No. SY02 (Aug. 15, 1988).

Helical Twist And Spontaneous Polarization Direction In Ferroelectric Smectic Liquid Crystals, 2-J. Am. Chem. Soc. 1986, 108, 4736–4742 (J. W. Goodby et al.).

A Chiral Induced Ferroelectric Liquid Crystal Phase Transition With A Vanishingly Small Enthalpy-Liquid Crystals, 1988, vol. 3, No. 9, 1245–1254 (J. W. Goodby et al.).

Tristable Switching In Surface Stabilized Ferroelectric Liquid Crystals With A Large Spontaneous Polarization-Japanese Journal of Applied Physics, vol. 27, No. 5, May, 1988, pp. L729–L732 (A. D. L. Chandani et al.).

Primary Examiner—Robert L. Stoll
Assistant Examiner—Shean C. Wu
Attorney, Agent, or Firm—Cushman, Darby & Cushman

[57] ABSTRACT

A new tetrastable liquid crystal is provided which is useful for display and switching devices. The liquid crystal has the formula

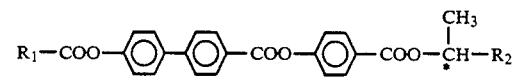

where $R_1$ is a $C_{5-18}$ alkyl group and $R_2$ is a $C_{4-15}$ alkyl group and * is an optically active center.

1 Claim, 5 Drawing Sheets

OPTICAL RESPONSE OF THE PRESENT TETRASTABLE LIQUID CRYSTAL

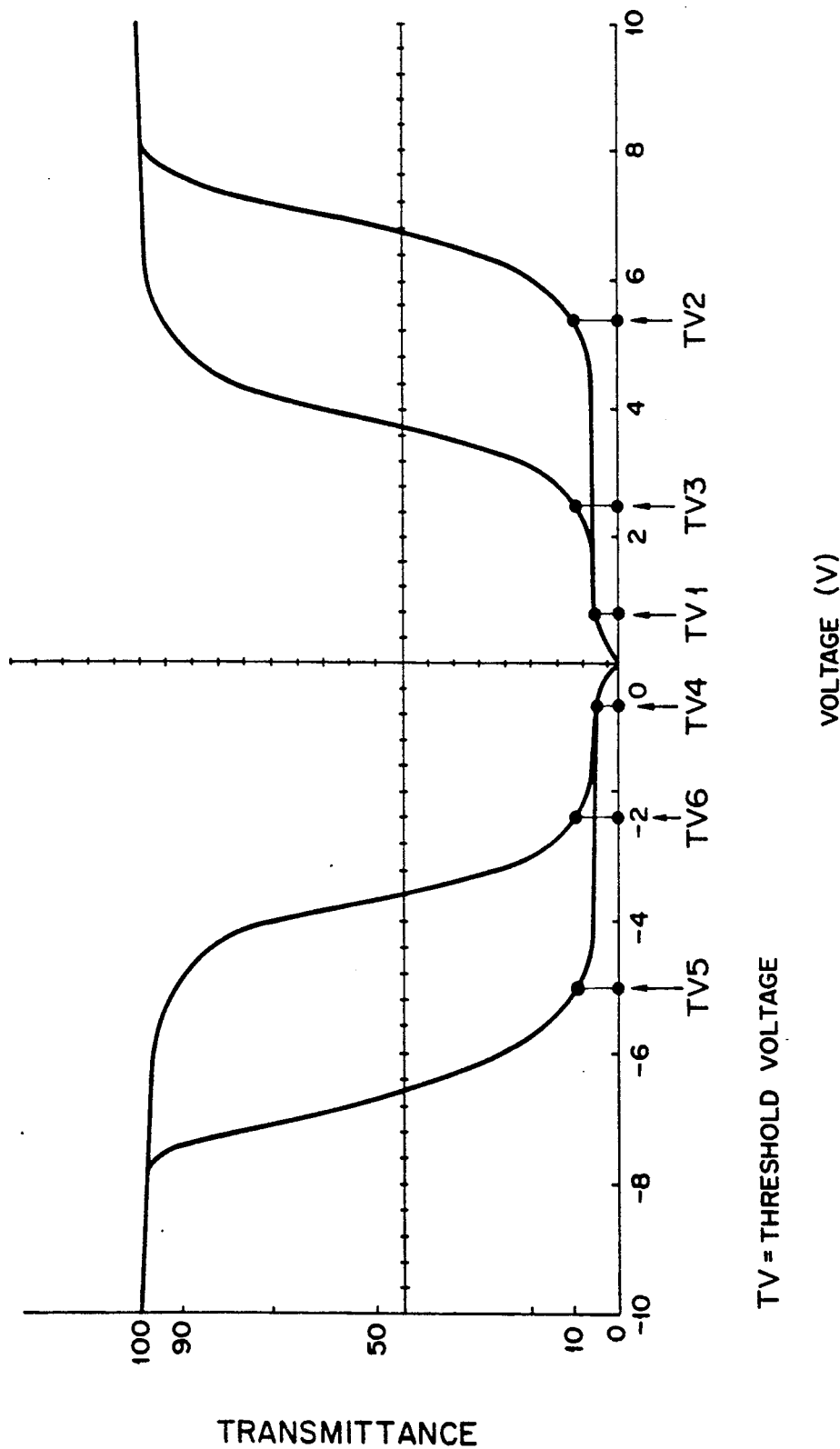

APPLIED TRIANGULAR WAVE

OPTICAL RESPONSE OF CONVENTIONAL NEMATIC LIQUID CRYSTAL

OPTICAL RESPONSE OF CONVENTIONAL BISTABLE LIQUID CRYSTAL

OPTICAL RESPONSE OF THE PRESENT TETRASTABLE LIQUID CRYSTAL

LIQUID CRYSTAL COMPOUND

The present invention relates to a ferroelectric chiral smectic liquid crystal compound particularly, to a ferroelectric liquid crystal compound which has four stable (tetrastable) molecular orientations or alignments and is useful for display devices or electro-optic devices utilizing response to electric fields.

There are electro-optic devices commercially available which use such nematic liquid crystals as DSM, TN, G-H or STN type. Their application fields, however, are not broad but rather limited, since their response speeds to electric field are not large, i.e., few micro second to some ten micro second. This is due to the fact that torque for moving their molecules is not large enough, since it is based, in principle, on anisotropy of dielectric constant. Under the circumstances, a ferroelectric liquid crystal is proposed which has such large response speed as few micro second to some ten micro second (Meyer et al: Le Journal de Physique, 36, 1975, L-69). The liquid crystal has spontaneous polarization (Ps) and its torque is based on Ps×E where E is an applied field. Another ferroelectric liquid crystal is proposed in the patent (JP 3-307837). These literatures are silent on tetrastable state referred to hereinafter.

There are high speed electro-optic devices which use ferroelectric liquid crystals. One of the devices is that a twisted structure is released by a wall force and then two molecular orientations which are in parallel with the wall are made to change by polarity of an applied field (JP 56-107216).

Figure 2:
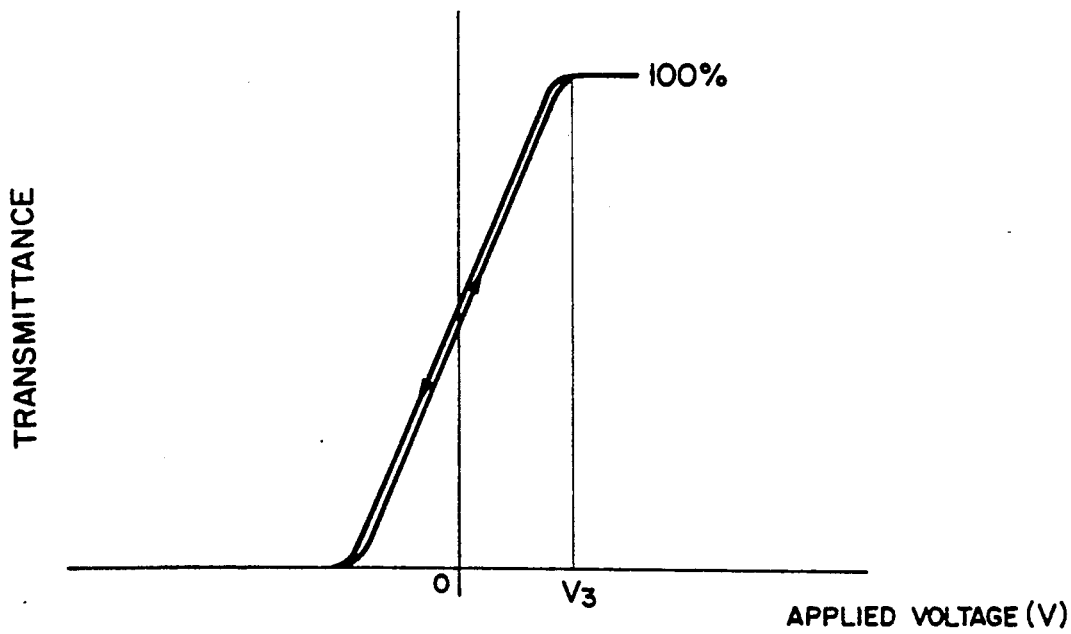
Figure 4A:
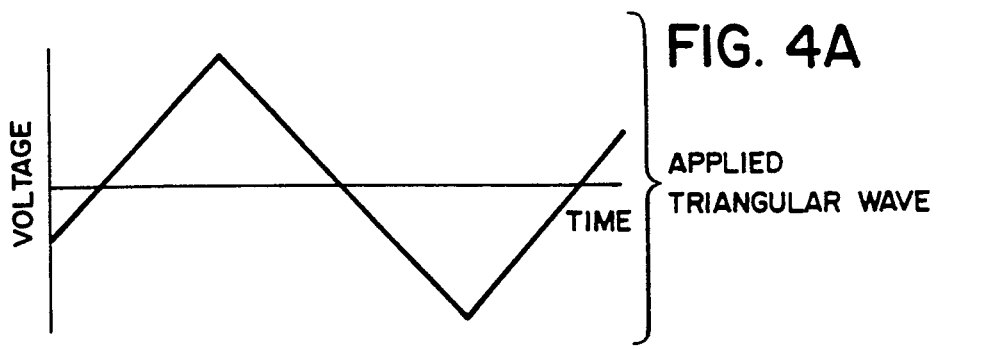
Figure 4B:
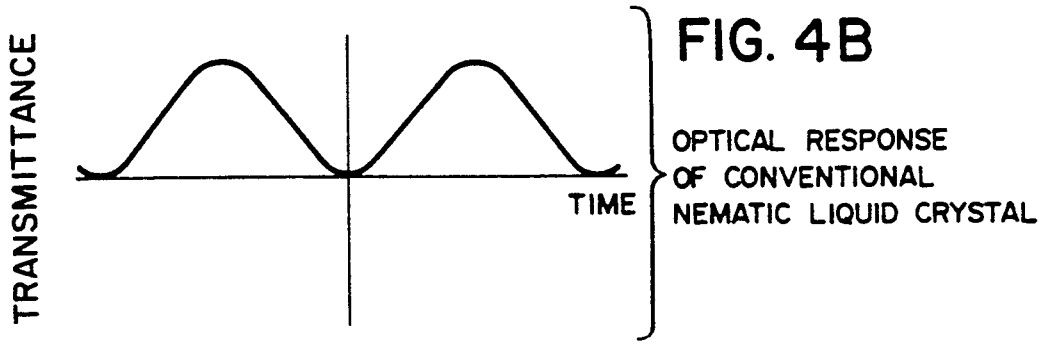
Figure 4C:
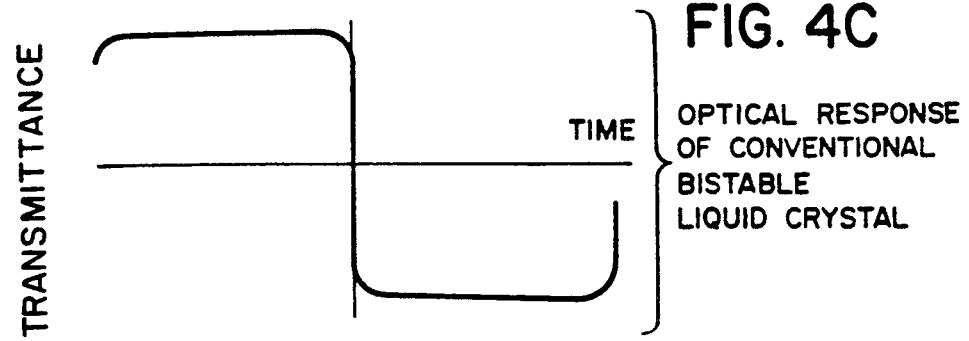
Figure 4D:
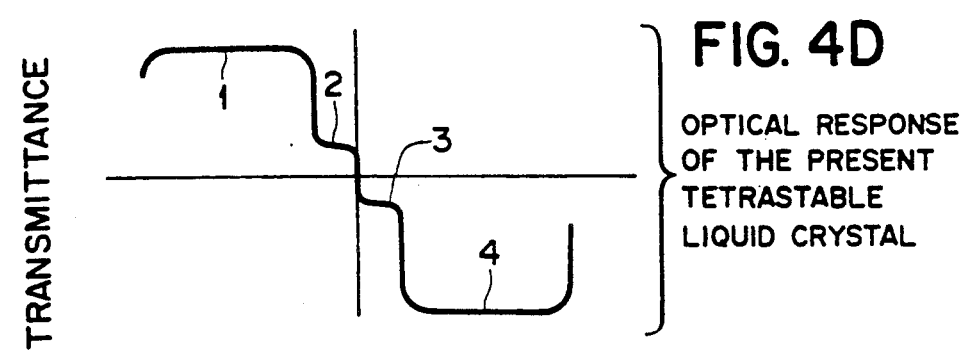
Figure 5:
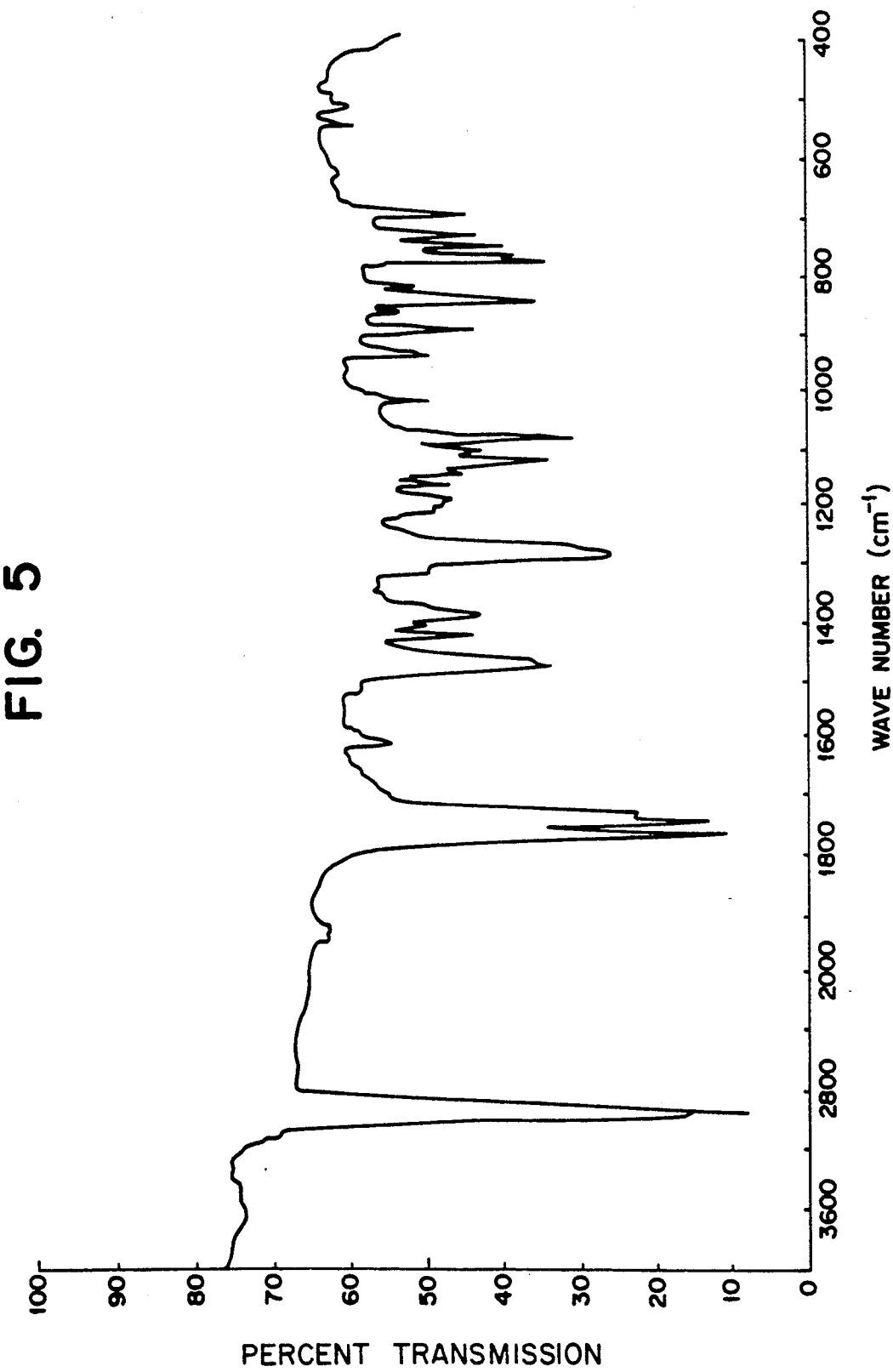
Figure 6:
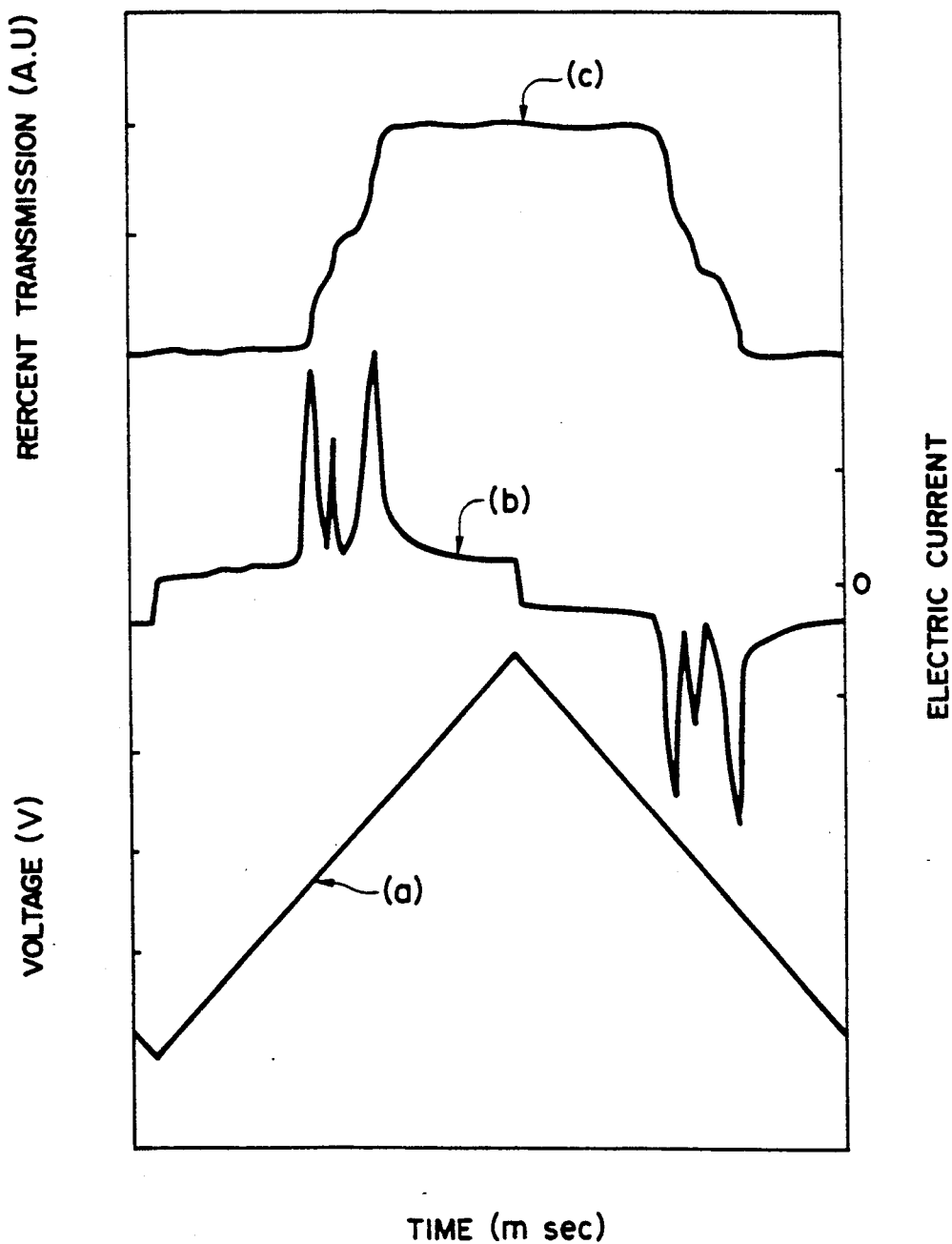

In the accompanying drawings,

FIG. 1 is percent transmission vs. applied voltage or hysteresis of ideal binary bistable state liquid crystals, FIG. 2 is the same hysteresis as above of binary bistable state liquid crystals actually synthesized, FIG. 3 is the same hysteresis as above of tetrastable state liquid crystals, FIG. 4(A) is voltage vs. time diagram of applied angular wave and FIGS. 4(B)–(D) are the same diagrams as above showing optical responses of commercially available nematic liquid crystals, binary bistable liquid crystals actually synthesized, and the present tetrastable state liquid crystals, respectively, FIG. 5 is an IR spectrum of the compound mentioned in example 1 of the present specification, and FIG. 6 is tetrastable switching or optical and electric response of the present compound wherein line (a) is a triangular wave voltage applied on liquid crystal electro-optic devices, line (b) is switching current peaks and line (c) is change in optical percent transmission (transmittance) according to the triangular wave voltage of the line (a).

The devices mentioned above are based on the premise that there is a compound having ideal bistable state whose electric field response wave form is illustrated in FIG. 1. However, no such compound having such ideal bistable state has been found yet but liquid crystals actually prepared of bistable state have electric field response waveform as shown in FIG. 2. When switching circuits for light are constructed with such compounds having such waveform as in FIG. 2, percent transmission (transmittance) gradually changes as change of an applied field from ⊖ to ⊕. Accordingly, a simple change in an applied field between "ON" and "OFF" does not work well. Furthermore, bistable liquid crystals actually prepared hardly produce ideal molecular orientation or monodomain structure at Sc* phase stage where no electric field is applied but rather produce disclination (fault) or twist or disturbance in molecular orientation, and appearance of the ideal bistable state in a large area is very difficult. Furthermore, contrast between brightness and darkness is degraded, and field of view is narrowed when dynamic addressing scheme is adopted, since the threshold value or voltage at which luminance changes with a given value is low. Conventional liquid crystals having bistable state actually prepared, are poor in memory effect, since hysteresis is not in the form of FIG. 1 but FIG. 2. Continuous application of voltage $V_3$ as shown in FIG. 2 or continuous application of high frequency is applied in order to maintain speed at the stable Sc* phase. In any case, a large loss in energy is encountered.

Although high speed liquid crystal electro-optic devices are desired which use strong interrelation between an applied field and molecular orientation in ferroelectric liquid crystals, the devices now available in the market have many problems left unsolved.

The present invention provides a novel liquid crystal compound which is able to be used in electro-optic devices where good contrast between brightness and darkness and stable molecular orientation are obtained when no electric field is applied and sharp threshold characteristics and clear hysteresis as shown in FIG. 3 are displayed. Furthermore, the present invention provides a novel liquid crystal in which dynamic addressing scheme is able to be adopted with ease and tetrastable state is achieved which makes high speed response possible.

The present liquid crystal is a novel tetrastable ferroelectric liquid crystal having chiral smectic phase which is different from the conventional bistable chiral smectic phase or Sc* phase.

The tetrastable state is illustrated as follows. To liquid crystal electro-optic devices where the first and the second electrode plates are arranged apart with a given distance, a ferroelectric liquid crystal is placed between the two plates and electric voltage in the triangular waveform is applied to the first and second electrode plates as shown in FIG. 4(A). The ferroelectric liquid crystal has molecular orientation of the first stable or the second stable state (FIG. 4 (D), 2 or 3) when no electric field is applied. When electric field is applied, molecular orientation has the third stable state (FIG. 4 (D), 1) which is different from the first or second stable state mentioned above, in one of directions of electric field, and further, has the fourth stable state (FIG. 4 (D), 4) which is different from any of the first, second and third stable states mentioned above, in the other direction of the electric field. The commercially available nematic liquid crystals and binary bistable liquid crystals actually synthesized have no such four stable states (FIG. 4 (B) and (C)).

According to the present invention, the compound having the formula mentioned below is provided.

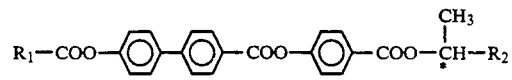

where $R_1$ is a $C_{5-18}$ alkyl group, $R_2$ is a $C_{4-15}$ alkyl group and * is optically active center consisting of methyl group.

Preference is a $C_{6-12}$ straight chain alkyl group for $R_1$ and a $C_{5-12}$ straight chain alkyl group for $R_2$.

One of the processes for preparing the compound is allowing 4-benzyloxybenzoic acid compound to react with optically active 2-alkanol to prepare 1-methylalkyl 4-benzyloxybenzoate, subjecting to hydrogenolysis to prepare 1-methylalkyl 4-hydroxybenzoates, followed by allowing the esters obtained to react with 4'-alkanoyl- oxybiphenyl-4-carboxylic acids in the presence of dicyclohexylcarbodiimide (DCC) until 1-methylalkyl 4'-alkanoyloxybiphenyl-4-carboxylates.

The present tetrastable state ferroelectric liquid crystals have unexpected advantage over the conventional nematic liquid crystals. That is, the conventional displays need complex driving system such as active matrix system. On the other hand, all that is necessary for the present tetrastable state ferroelectric liquid crystal is a simple matrix display. Accordingly, the conventional displays need complex steps for production, and expenses. Difficulties are encountered for production of displays of large scale. On the other hand, a display using the present liquid crystal is produced in a simple manner and inexpensive. Displays of large scale are able to be made.

EXAMPLE 1

1) Synthesis of 1-methylheptyl 4-benzyloxybenzoate

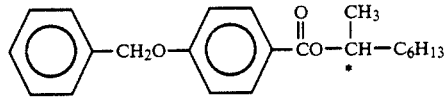

To a solution of 4-benzyloxybenzoic acid chloride (1.23 g) in methylene chloride (10 ml) was added slowly under ice cooling a solution of optically active 2-octanol (0.59 g), dimethylaminopyridine (0.55 g) and triethylamine (0.48 g) in methylene chloride (20 ml). The mixture was left to stand until it reached room temperature and was left to stand overnight in order to complete the reaction. The solution was poured in ice water and extracted with methylene chloride. The extracted layer was washed with dilute hydrochloric acid, water, 1N aqueous sodium carbonate solution and water, in this order, and dried over anhydrous magnesium sulfate. After the extract was distilled to remove the solvent until a crude product was obtained, the product was purified by toluene-silica gel column chromatography and further recrystallized from ethanol to obtain the titled compound (1.48 g).

2) Synthesis of 1-methylheptyl-4-hydroxybenzoate

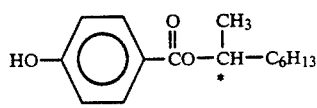

To a solution of the compound obtained in 1) above in ethanol (15 ml) was added 10% Pd on carbon (0.36 g) and the mixture was hydrogenated under a hydrogen atmosphere to obtain the titled compound (1.29 g).

3) Synthesis of 4-(1-methylheptyloxycarbonyl)phenyl 4'-n-nonanoyloxybiphenyl-4-carboxylate and observation of phase transition temperatures

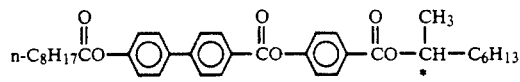

To a solution of 4'-nonanoyloxybiphenyl-4-carboxylic acid (5.00 g) and the compound obtained in 2) above (6.76 g) in dry tetrahydrofuran (330 ml) were added dicyclohexylcarbodiimide (DCC, 6.18 g) and dimethylaminopyridine (0.24 g). After the solution was stirred overnight, it was filtered. The filtrate obtained was distilled to remove the tetrahydrofuran. The residue was dissolved in methylene chloride and washed with a small amount of water. The methylene chloride layer was collected and dehydrated over anhydrous magnesium sulfate. The solution was distilled to remove the methylene chloride. The residue was purified by silica gel column chromatography and recrystallized from ethanol, to obtain the titled compound (2.83 g).

Phase transition temperatures (°C.) which were observed under a polarization microscope with a hot stage were as follows:

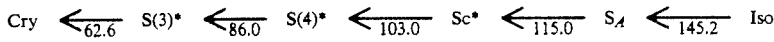

where S(3)*: ternary tristable state,
S(4)*: tetrastable state.

FIG. 5 is an IR spectrum (KBr) of the titled compound. Specific rotation $[\alpha]_D^{25} = -20.9°$.

EXAMPLE 2

In a liquid crystal cell of 1.9 μm thick in which orientated film of polyimide which had been subjected to rubbing was placed on an ITO electrode plate was filled with liquid crystal of Isotropic phase obtained in Example 1.

The liquid crystal cell was placed in a polalization microscope having a photomultiplier where two light-polarizing plates are on cross axis, so that a polarizer was over a parallel axis of a molecule when minus voltage was applied at an SA phase. The liquid crystal cell was slowly cooled to an Sc* phase with 0.1–1.0 °C./min. of thermal gradient. Further cooling was made and triangular voltage ±30 V, 10 Hz was applied at temperature range of 103.0° to 86.0° C. (FIG. 6). Percent transmission changed in four stages (C), i.e., from darkness at applied voltage of the minus range to brightness at applied voltage of the plus range, via two intermediates at applied voltage of zero volt. According to the change, switching current peak (b) appeared. This supports the fact that there are four stable orientations or alignments of liquid crystal molecule.

The present liquid crystal is useful for display and switching devices using the same.

We claim:
1. A compound of the formula

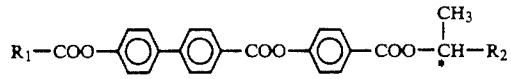

wherein $R_1$ is a $C_{5-18}$ alkyl group, $R_2$ is a $C_{4-15}$ alkyl group and * is an optically active center, which compound is in the S(4)* phase showing tetrastable states.

* * * * *